US008660643B2

(12) United States Patent
Gunderson

(10) Patent No.: US 8,660,643 B2
(45) Date of Patent: Feb. 25, 2014

(54) NON-SUSTAINED TACHYARRHYTHMIA ANALYSIS TO IDENTIFY LEAD RELATED CONDITION

(75) Inventor: Bruce D. Gunderson, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 13/569,354

(22) Filed: Aug. 8, 2012

(65) Prior Publication Data

US 2012/0296386 A1 Nov. 22, 2012

Related U.S. Application Data

(63) Continuation of application No. 12/606,899, filed on Oct. 27, 2009, now Pat. No. 8,260,419.

(51) Int. Cl.
A61N 1/365 (2006.01)

(52) U.S. Cl.
USPC .......................................................... 607/14

(58) Field of Classification Search
None
See application file for complete search history.

(56) References Cited

U.S. PATENT DOCUMENTS

| 4,374,382 | A | 2/1983 | Markowitz |
| 5,545,186 | A | 8/1996 | Olson et al. |
| 5,755,736 | A | 5/1998 | Gillberg et al. |
| 5,776,168 | A | 7/1998 | Gunderson |
| 6,393,316 | B1 | 5/2002 | Gillberg et al. |
| 7,047,083 | B2 | 5/2006 | Gunderson et al. |
| 7,167,747 | B2 | 1/2007 | Gunderson et al. |
| 7,236,828 | B2 | 6/2007 | Casavant et al. |
| 7,289,851 | B2 | 10/2007 | Gunderson et al. |
| 7,333,855 | B2 | 2/2008 | Gunderson et al. |
| 7,369,893 | B2 | 5/2008 | Gunderson |
| 7,539,540 | B2 | 5/2009 | Gunderson et al. |
| 7,567,835 | B2 | 7/2009 | Gunderson et al. |
| 7,974,690 | B2 | 7/2011 | Kracker |
| 2004/0064062 | A1 | 4/2004 | Zhou et al. |
| 2004/0064161 | A1 | 4/2004 | Gunderson et al. |
| 2004/0162593 | A1 | 8/2004 | Jorgenson et al. |
| 2005/0137636 | A1 | 6/2005 | Gunderson et al. |
| 2005/0154421 | A1 | 7/2005 | Ousidigian |
| 2006/0155338 | A1 | 7/2006 | Mongeon et al. |
| 2006/0247706 | A1 | 11/2006 | Germanson et al. |

FOREIGN PATENT DOCUMENTS

WO 2009/148429 A1 12/2009

OTHER PUBLICATIONS

Danilovic et al., "Pacing Impedance Variability in Tined Steroid Eluting Leads," PACE, Blackwell Futura Publishing, Malden, MA, US, vol. 21, No. 7, Jul. 1, 1998, pp. 1356-1363.
International Preliminary Report on Patentability from corresponding PCT Application No. PCT/US2010/033399 dated Feb. 24, 2012, (13 pages).
Reply to Written Opinion from corresponding PCT Application Serial No. PCT/US2010/033399 filed Feb. 14, 2011 (10 pages).
International Search Report and Written Opinion of international application No. PCT/US2010/033399, mailed Aug. 27, 2010, 13 pp.

Primary Examiner — Carl H Layno
Assistant Examiner — Paula J Stice
(74) Attorney, Agent, or Firm — Michael J. Ostrom

(57) ABSTRACT

Techniques for determining whether a lead related condition exists based on analysis of a cardiac electrical signal associated with a non-sustained tachyarrhythmia (NST) are described. In some examples, the techniques include determining the duration of intervals between consecutive cardiac events, e.g., R-R intervals, during an NST. The techniques may further include determining one or more metrics based on the durations of the intervals during the NST. Examples of metrics include an average, a minimum, a maximum, a range, a median, a mode, or a mean. A lead related condition is identified based on the values of the one or more metrics, e.g., by comparison to respective thresholds. In some examples, an alert is provided or a therapy modification is suggested if a lead related condition is identified.

18 Claims, 9 Drawing Sheets

NON-SUSTAINED TACHYARRHYTHMIA ANALYSIS TO IDENTIFY LEAD RELATED CONDITION

This application is a continuation of U.S. application Ser. No. 12/606,899, filed on Oct. 27, 2009 and issued as U.S. Pat. No. 8,260,419 on Sep. 4, 2012, the content of which is incorporated herein by reference in its entirety

TECHNICAL FIELD

The disclosure relates to implantable medical devices, and, more particularly, to collection and analysis of diagnostic information by medical devices.

BACKGROUND

A variety of implantable medical devices for delivering a therapy and/or monitoring a physiological condition have been clinically implanted or proposed for clinical implantation in patients. Some implantable medical devices deliver electrical stimulation to, and/or monitor conditions associated with, the heart, muscle, nerve, brain, stomach or other organs or tissue. Some implantable medical devices employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as signal generation and/or sensing circuitry.

Some implantable medical devices, such as cardiac pacemakers or cardioverter-defibrillators, provide therapeutic electrical stimulation to the heart via electrodes carried by one or more implantable leads. The electrical stimulation may include signals such as pulses or shocks for pacing, cardioversion, or defibrillation. In some cases, an implantable medical device senses intrinsic depolarizations of the heart, and controls delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Implantable medical leads associated with an implantable medical device typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within an associated implantable medical device housing to respective electrodes or sensors. Some electrodes may be used for both stimulation and sensing. Each electrical conductor is typically electrically isolated from other electrical conductors, and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in leads or connections may result in intermittent or continuous short circuits, open circuits, or changes in lead impedance.

Short circuits, open circuits, or significant changes in impedance may be referred to, in general, as lead related conditions. In the case of cardiac leads, sensing of an intrinsic heart rhythm through a lead can be altered by lead related conditions. Structural modifications to leads, conductors, or electrodes may alter sensing integrity. Furthermore, impedance changes in the stimulation path due to lead related conditions may affect sensing and stimulation integrity for pacing, cardioversion, or defibrillation.

In addition to lead related conditions, conditions associated with sensor devices or sensing circuitry, as well as conditions associated with electrodes or sensors not located on leads, may affect sensing integrity. Furthermore, T-wave oversensing, where the implantable medical device misidentifies T-waves as P-waves or R-waves, oversensing due to ambient radiofrequency noise, oversensing due to patient movement artifacts, or other oversensing or undersensing issues, which may be unrelated to the integrity of implantable leads or other medical device components, may affect sensing integrity.

SUMMARY

In general, the disclosure is directed to techniques for determining whether a lead related condition exists based on analysis of a cardiac electrical signal associated with a non-sustained tachyarrhythmia (NST). More particularly, the techniques include determining the duration of intervals between consecutive cardiac events, e.g., R-R intervals, during an NST. The techniques further include determining one or more metrics based on the durations of the intervals during the NST. Examples of metrics include an average, a minimum, a maximum, a range, a median, a mode, or a mean. A lead related condition is identified based on the values of the one or more metrics, e.g., by comparison to respective thresholds. In some examples, an alert is provided, or a therapy or sensing modification is automatically performed or suggested if a lead related condition is identified.

In one example, a method comprises detecting a plurality of cardiac events based on a cardiac electrical signal, measuring a plurality of intervals between consecutive ones of the detected cardiac events, detecting a non-sustained tachyarrhythmia based on a subset of the measured intervals meeting a non-sustained tachyarrhythmia criterion, calculating at least one metric based on the subset of the measured intervals after detecting the non-sustained tachyarrhythmia, and identifying a lead integrity issue based on the at least one metric.

In another example, a system comprises an electrical sensing module that receives a cardiac electrical signal from a plurality of electrodes and detects a plurality of cardiac events based on the cardiac electrical signal, an interval measurement module that measures a plurality of intervals between consecutive ones of the detected cardiac events, a non-sustained tachyarrhythmia detection module that detects a non-sustained tachyarrhythmia based on a subset of the measured intervals meeting a non-sustained tachyarrhythmia criterion, a calculation module that calculates at least one metric based on the subset of the measured intervals after the detection of the non-sustained tachyarrhythmia, and a lead integrity evaluation module that identifies a lead integrity issue based on the metric.

In another example, a system comprises means for detecting a plurality of cardiac events based on a cardiac electrical signal, means for measuring a plurality of intervals between consecutive ones of the detected cardiac events, means for detecting a non-sustained tachyarrhythmia based on a subset of the measured intervals meeting a non-sustained tachyarrhythmia criterion, means for calculating at least one metric based on the subset of the measured intervals after detecting the non-sustained tachyarrhythmia, and means for identifying a lead integrity issue based on the at least one metric.

In another example, a computer readable storage medium comprises instructions that cause a processor to detect a plurality of cardiac events based on a cardiac electrical signal, measure a plurality of intervals between consecutive ones of the detected cardiac events, detect a non-sustained tachyarrhythmia based on a subset of the measured intervals meeting a non-sustained tachyarrhythmia criterion, calculate at least one metric based on the subset of the measured intervals after detecting the non-sustained tachyarrhythmia, and identify a lead integrity issue based on the at least one metric.

DETAILED DESCRIPTION

Figure 1:
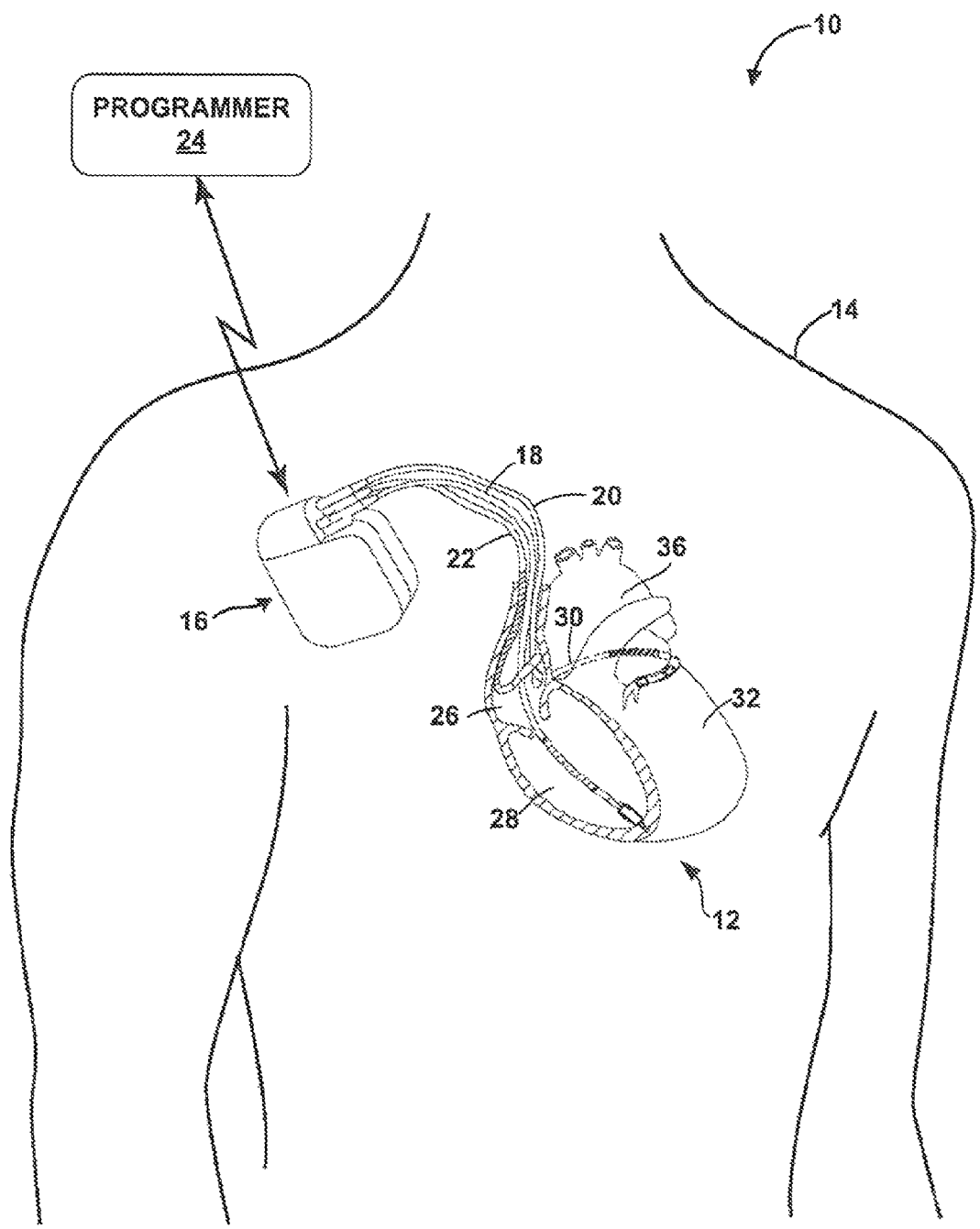
FIG. 1 is a conceptual diagram illustrating an example system comprising an implantable medical device (IMD) for sensing the electrical activity of a heart of patient and/or delivering electrical stimulation therapy to the heart via implantable leads.

FIG. 1 is a conceptual diagram illustrating an example system 10 that monitors and/or provides therapy to a heart 12 of a patient 14. System 10 includes implantable medical device (IMD) 16, which is coupled to implantable leads 18, 20 and 22. IMD 16 may be, for example, an implantable pacemaker, cardioverter, and/or defibrillator that senses electrical activity within heart 16 and provides electrical signals to heart 12 via electrodes coupled to leads 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12.

In some alternative embodiments, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. In some examples, IMD 16 provides pacing pulses as part of a cardiac resynchronization therapy (CRT) or anti-tachycardia pacing therapy (ATP).

IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver ATP, or cardioversion or defibrillation therapy, to heart 12 in the form of electrical pulses. In some examples, IMD 16 may be programmed to deliver a progression of therapies, e.g., ATP followed by defibrillation, or pulses with increasing energy levels, until a tachyarrhythmia of heart 12 is stopped. IMD 16 detects tachycardia or fibrillation employing one or more tachycardia or fibrillation detection techniques known in the art.

In the example of FIG. 1, system 10 also includes a programmer 24. In some examples, programmer 24 may be a handheld computing device, computer workstation, or networked computing device. A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver defibrillation pulses, select waveforms for the defibrillation pulses, or select or configure a fibrillation detection algorithm for IMD 16. The user may also use programmer 24 to program similar aspects of other therapies provided by IMD 16, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 is an example of a device that detects a non-sustained tachyarrhythmia (NST), and subsequently determines whether a lead related condition exists based on analysis of a cardiac electrical signal associated with the NST. In some examples, IMD 16 determines one or more metrics based on analysis of the cardiac electrical signal associated with the NST. Additionally, IMD 16 may compare the metrics to a previously determined threshold to determine whether a lead related condition exists. In some examples, IMD 16 may automatically perform a therapy or sensing modification if IMD 16 determines that a lead related condition exists. Additionally or alternatively, programmer 24 may receive and display an alert or a suggestion for therapy or sensing modifications to a user if IMD 16 determines that a lead related condition exists.

In other examples, one or more devices other than IMD 16 may, alone, or in combination with IMD 16, implement the techniques described herein. For example, programmer 24 or another external device may receive an electrogram (EGM) or other data related to a cardiac electrical signal from IMD 16 and may detect a NST by analyzing the data. Programmer 24 or another external device may then analyze the data and determine whether a lead related condition exists based on the analysis. Subsequently, programmer 24 or another external device may display an alert or suggestion for therapy or sensing modification to a user, or may automatically modify the therapy or sensing provided by IMD 16. Furthermore, in some examples, the medical device and/or leads are not implanted.

Figure 2:
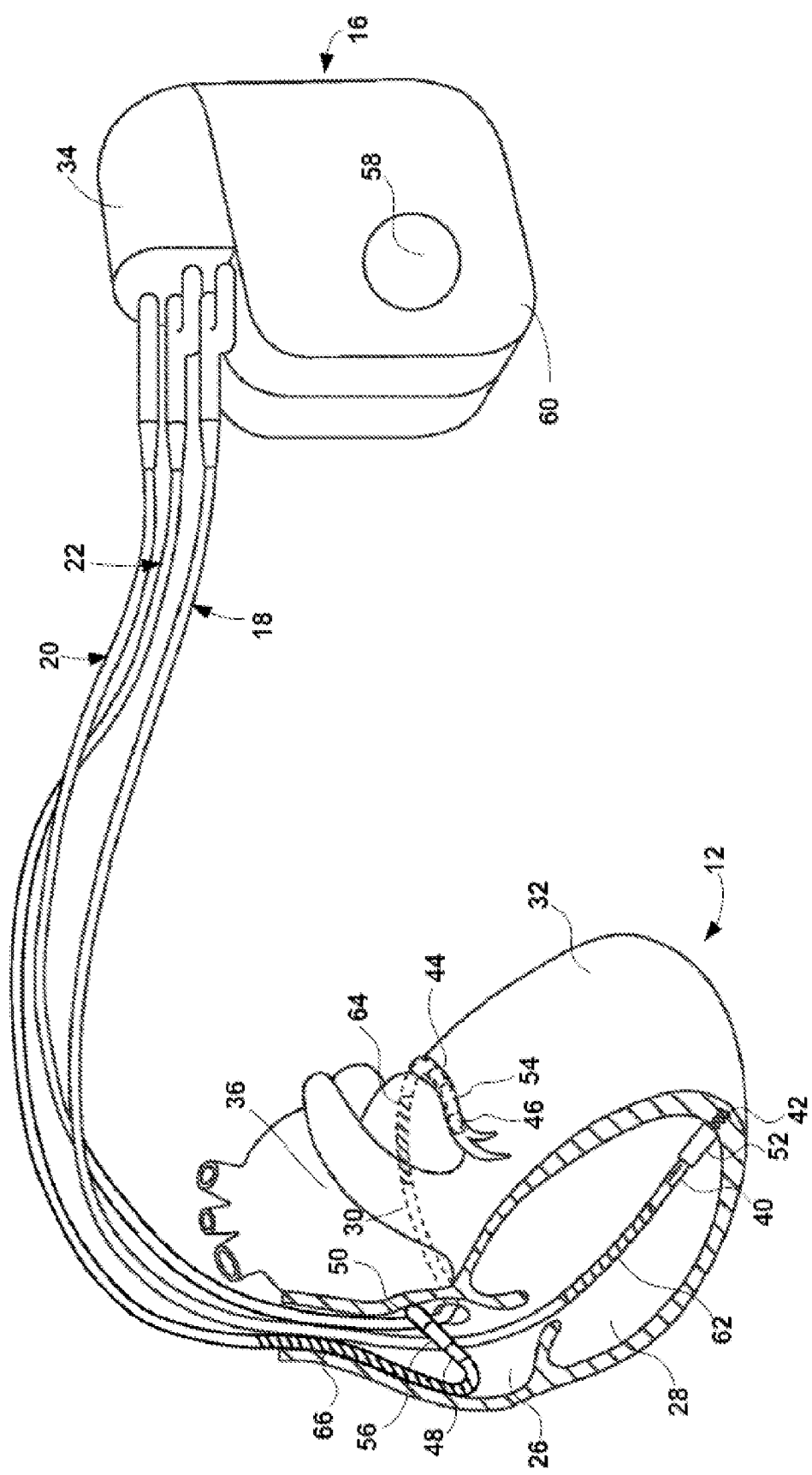
FIG. 2 is a conceptual diagram further illustrating the IMD and leads of the system of FIG. 1 in conjunction with the heart.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36 in the illustrated example, but other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some embodiments may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode may be configured as appropriate for the application of the sensing electrode configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. In some examples, IMD 16 delivers pacing pulses to one or both of the RV or LV to provide CRT. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3.

Figure 3:
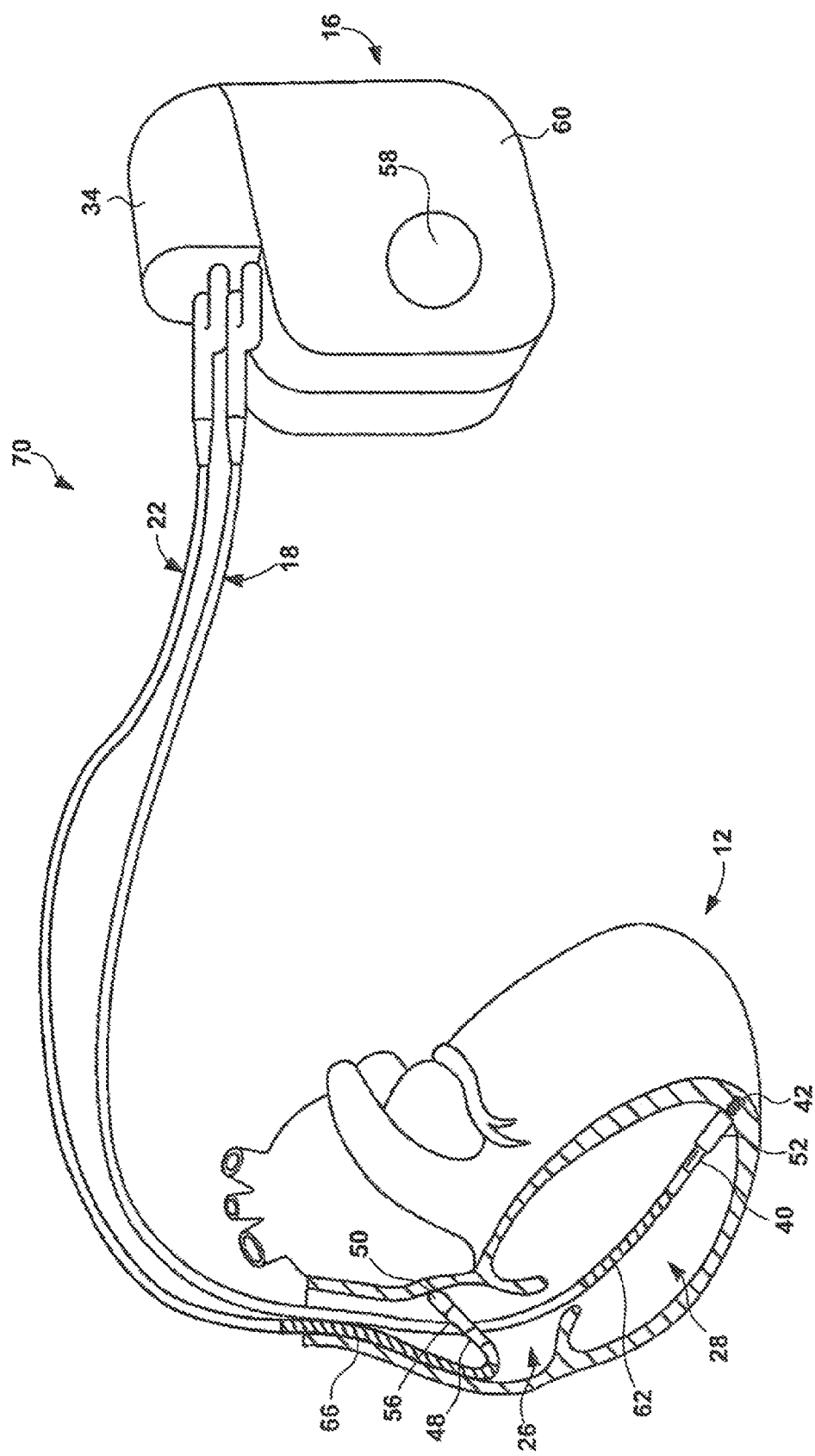
FIG. 3 is a conceptual diagram illustrating another example therapy system comprising the IMD of FIG. 1 coupled to a different configuration of leads.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Analysis of cardiac electrical signals according to the techniques described herein may also be performed by or with respect to system 70.

Figure 4:
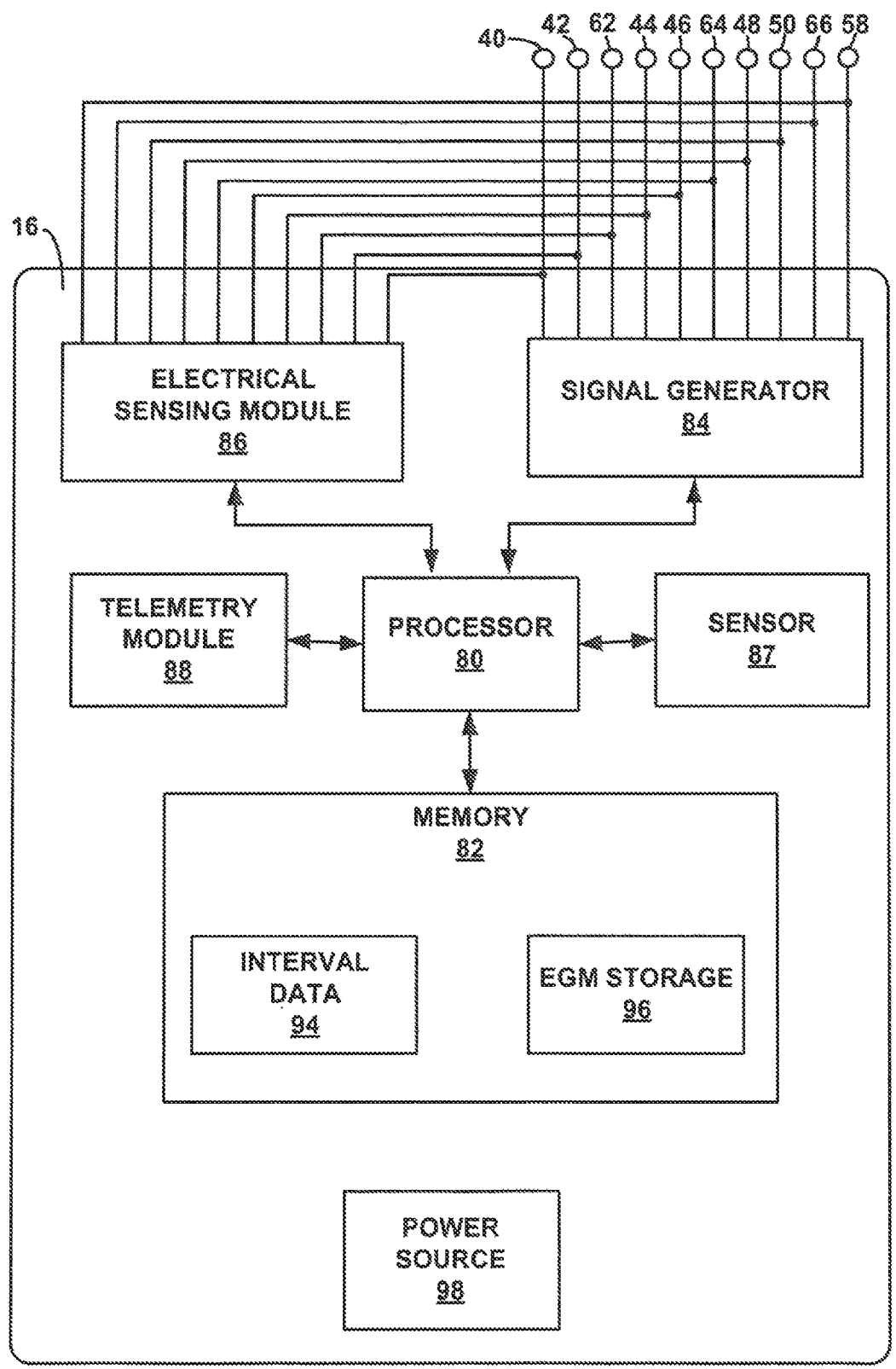
FIG. 4 is a functional block diagram illustrating an example configuration of the IMD of FIG. 1.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), static random access memory (SRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12. Processor 80 may control signal generator 84 to deliver stimulation according to a selected one or more therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver pacing, cardioversion, or defibrillation pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing electrode configuration, via the switch module within electrical sensing module 86, e.g., by providing signals via a data/address bus. Electrical sensing module 86 may include multiple detection channels, each of which may comprise an amplifier. In response to the signals from processor 80, the switch module of electrical sensing module 86 may couple selected electrodes to each of the detection channels.

Sensing module 86 may include one or more detection channels, each of which may comprise an amplifier. The detection channels may be used to sense cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, some various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the sensing electrodes that are selected for coupling to this wide-band amplifier may be converted to multi-bit digital signals by an analog-to-digital converter (ADC) provided by, for example, sensing module 86 or processor 80. In some examples, processor 80 may store the digitized versions of signals from the wide band channel in electrogram (EGM) storage 96 of memory 82. Processor 80 may employ digital signal analysis techniques to characterize the digitized signals from the wide band channel to, for example detect and classify the patient's heart rhythm. Processor 80 may detect and classify the patient's heart rhythm by employing any signal processing methodologies appropriate for the intended application or applications of IMD 16.

Processor 80 may maintain programmable counters which, if IMD 16 is configured to generate and deliver pacing pulses to heart 12, may control the basic time intervals associated with various modes of single and dual chamber pacing, including CRT. Intervals defined by processor 80 may include atrial and ventricular pacing escape intervals, V-V intervals for CRT, refractory periods during which sensed P-waves and R-waves are ineffective to restart timing of the escape intervals, and the pulse widths of the pacing pulses. The durations of these intervals may be determined by processor 80 in response to stored data in memory 82.

Interval counters maintained by processor 80, such as escape interval counters for pacing, may be reset upon sensing of R-waves and P-waves with detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by signal generator 84, and thereby control the basic timing of cardiac pacing functions, including CRT and ATP.

The value of the count present an interval counter when reset by sensed R-waves and P-waves may be used by processor 80 to measure the durations of R-R intervals, P-P intervals, P-R intervals and R-P intervals, which are measurements that may be stored in memory 82 as interval data 94. Processor 80 may use the count in the interval counters to detect a tachyarrhythmia event, such as an atrial or ventricular fibrillation or tachycardia. Processor 80 may also use the count in the interval counters to detect non-sustained tachyarrhythmias (NSTs) based on R-R or P-P intervals. A portion of memory 82 may be configured as a plurality of recirculating buffers, capable of holding series' of measured intervals, which may be analyzed by processor 80 to determine whether the patient's heart 12 is presently exhibiting atrial or ventricular tachyarrhythmia, or whether a NST is detected.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NONLETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian are incorporated herein by reference in their entireties. However, other arrhythmia detection methodologies may also be employed by processor 80 in other examples.

IMD 16 may comprise one or more sensors, such as sensor 87 illustrated in the example of FIG. 4. Sensor 87 may be within housing 60 (FIG. 2) of IMD 16. IMD 16 may additionally or alternatively be coupled to one or more sensors located outside of housing 60 of IMD 16. Sensor 87 may be located on or within one or more of leads 18, 20 and 22, or another lead which may or may not include stimulation/sensing electrodes. In some examples, sensor 87 may be separately housed from IMD 16, and may be coupled to IMD 16 via wireless communication. Sensor 87 may be implanted or external.

Sensor 87 may comprise, as examples, a pressure sensor, a motion sensor, a heart sound sensor, or any sensor capable of generating a signal that varies a function of mechanical activity, e.g., contraction, of heart 12. A pressure sensor may be, for example, a capacitive pressure sensor that senses an intracardiac or other cardiovascular pressure. A motion sensor may be, for example, an accelerometer or piezoelectric element. Processor 80 may receive one or more signals from sensor 87 or a plurality of sensors. Processor 80 may monitor, among other things, the mechanical activity of heart 12 based on such signals.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus.

In some examples, processor 80 may transmit atrial and ventricular heart signals produced by atrial and ventricular sense amplifier circuits within electrical sensing module 86, e.g., narrow band or wide band sense amplifier circuits, to programmer 24. Processor 80 may store data related to a cardiac electrical signal within memory 82, and retrieve stored data from memory 82. Processor 80 may also generate and store marker codes indicative of different cardiac events that electrical sensing module 86 detects, such as ventricular and atrial depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, processor 80 is configured to detect or identify whether a lead related condition exists using any of the techniques described herein. For example, processor 80 may analyze the signals from electrical sensing module 86 to detect NSTs, and calculate one or more metrics based on the cardiac electrical signals during the NSTs. Processor 80 may then evaluate the calculation and may identify a lead related condition based on the evaluation. Programmer 24 may interrogate IMD 16 to receive the results of the evaluation, or processor 80 may send the results of the evaluation to programmer 24 or to another external device. In other examples, an external device, such as programmer 24, may analyze the signals to detect NSTs, calculate a metric based on the signals of the NSTs, and evaluate the calculation to determine whether a lead related condition exists.

Processor 80 may detect NSTs based on the durations of intervals between cardiac events in consecutive cardiac cycles, e.g., the durations of R-R intervals in the case of R-waves. As discussed above, such interval durations may be stored as interval data 94 in memory 82. Processor 80 may detect a NST based on a specific NST criterion. For example, if a subset of the measured intervals meets predetermined NST criteria (e.g., an interval duration threshold), processor 80 may determine that a NST exists or has occurred.

In some examples, processor 80 additionally or alternatively identifies a NST based on a morphological analysis of signals received from electrical sensing module 86 during the NST, which may distinguish between noise and cardiac depolarizations. For example, a morphological analysis may include any one or more of an amplitude regularity analysis, an analysis of the width of the QRS complex or other features of the EGM, or an analysis of slew rates. In some examples, a morphological analysis may involve a wavelet analysis, such as those described in U.S. Pat. No. 6,393,316, entitled "METHOD AND APPARATUS FOR DETECTION AND TREATMENT OF CARDIAC ARRHTHMIAS," which issued to Gillberg et al. on May 21. 2002, and U.S. Pat. No. 7,176,747, entitled "IDENTIFICATION OF OVERSENSING USING SINUS R-WAVE TEMPLATE," which issued to Gunderson et al. on Jan. 23, 2007. In some examples, the analysis may include the far-field EGM analysis techniques described in U.S. Pat. No. 7,333,855 to Gunderson et al., entitled "METHOD AND APPARATUS FOR DETERMINING OVERSENSING IN A MEDICAL DEVICE," which issued on Feb. 19, 2008. The entire content of each of U.S. Pat. Nos. 6,393,316, 7,176,747 and 7,333,855 is incorporated herein by reference in their entirety.

In some examples, a processor 80 additionally or alternatively identifies a NST based on the presence or absence of a confirmatory indication of tachyarrhythmia from one or more other sensing channels or sensors 87. Another sensing channel may include a different sensing electrode configuration than the primary sensing electrode configuration used by electrical sensing module 86 to detect a cardiac signal during the NST, and/or different signal processing circuitry, e.g., a different channel or amplifier, of sensing module 86. Processor 80 may detect mechanical activity (e.g., contraction) of heart 12 based on the signals provided by one or more sensors 87, and processor 80 may determine whether cardiac depolarizations detected by electrical sensing module 86 are correlated with mechanical activity of the heart to determine whether a NST has occurred.

In some examples, processor 80 determines whether a lead related condition exists based on characteristics of the cardiac electrical signal during one or more NSTs. For example, processor 80 may access interval data 94 in order to, for example, calculate one or more metrics based on the interval data for the cardiac electrical signal during the NST, e.g., based R-R intervals during the NST. Processor 80 may identify a lead related condition based on the metric, e.g., by comparison to a threshold. In response to determining that a lead related condition exists, processor 80 may notify a user (e.g., a patient or clinician) by, for example, activating an audible or vibratory alert mechanism within or coupled to IMD 16, or sending an alert via telemetry module 88 to, for example, programmer 24 (FIG. 1). Additionally or alternatively, processor 80 may instruct electrical sensing module 86 to perform a sensing modification and/or signal generator 84 to perform a therapy modification.

The various components of IMD 16 are coupled to power source 98, which may include a rechargeable or non-rechargeable battery. A non-rechargeable battery may be capable of holding a charge for several years, while a rechargeable battery may be inductively charged from an external device, e.g., on a daily or weekly basis.

Figure 5:
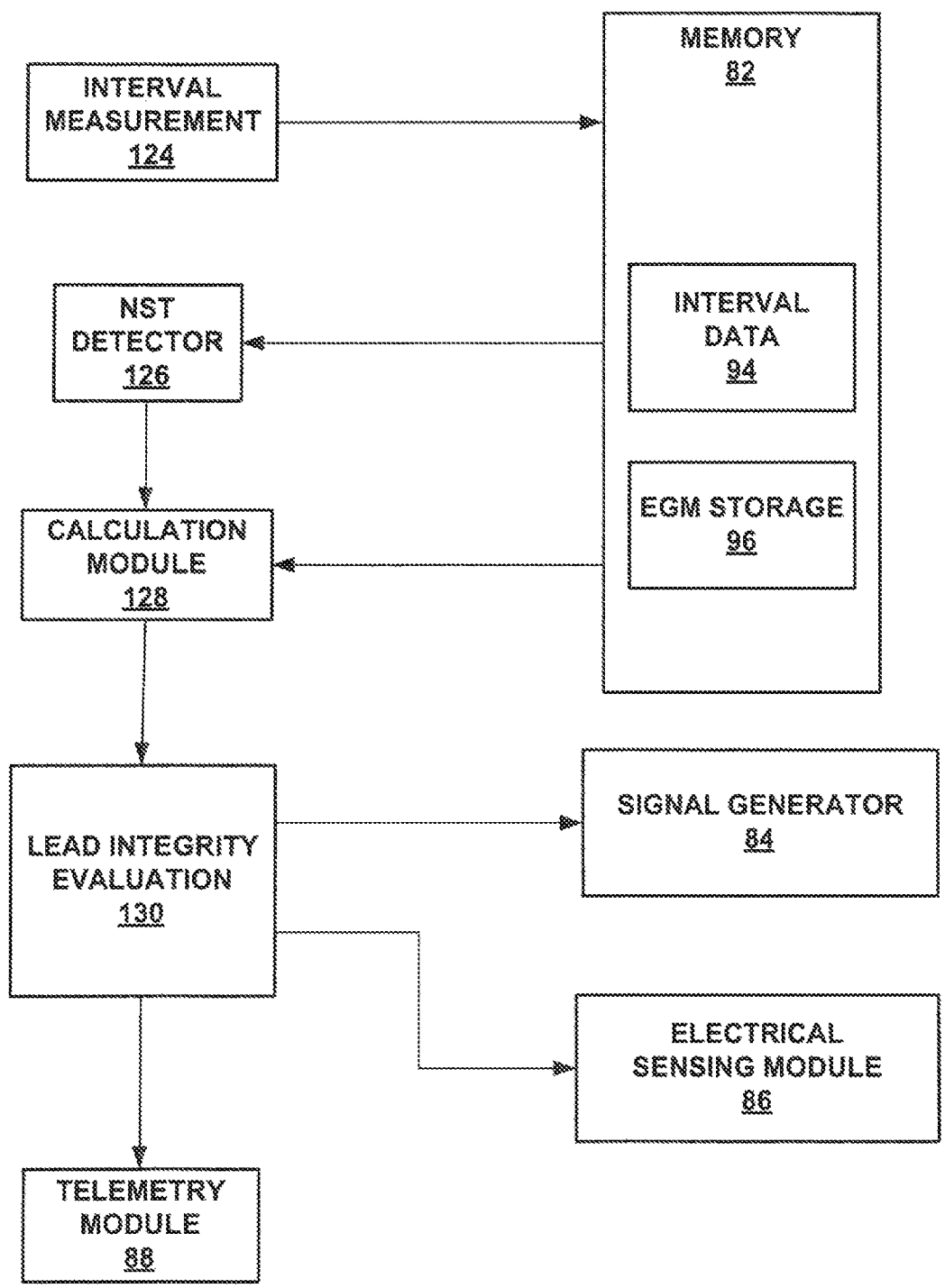
FIG. 5 is a functional block diagram illustrating a lead integrity evaluation module and other associated modules that determine whether a lead related condition exists.

FIG. 5 is a functional block diagram illustrating a lead integrity evaluation module 130 and other associated modules that determine whether a lead related condition exists according to one example implementation of the techniques described herein. In general, lead integrity evaluation module 130 determines whether a lead related condition exists based on characteristics of one or more cardiac electrical signals sensed by electrical sensing module 86 (FIG. 4) during one or more NSTs. In the example described with reference to FIG. 5, lead integrity evaluation module 130 determines whether a lead related condition exists based on R-R intervals during one or more NSTs. Along with lead integrity evaluation module 130, interval measurement module 124, NST detector module 126 and calculation module 128 may be implemented as software and/or hardware modules of processor 80 of IMD 16. In other examples, some or all of interval measurement module 124, NST detector module 126, calculation module 128 and lead integrity evaluation module 130 are implemented as hardware and/or software modules of one or more other devices, e.g., programmer 24 or other external or remote devices, or one or more processors of such other devices.

As discussed above, memory 82 stores data related to the one or more cardiac signals sensed by electrical sensing module 86 during one or more NSTs. For example, interval data 94 may include durations of one or more cardiac event intervals, e.g., R-R intervals, of the cardiac electrical signal sensed by electrical sensing module 86 during one or more NSTs. The durations of the cardiac event intervals may be determined by interval measurement module 124 based on indications received from electrical sensing module 86. EGM storage 96 may store EGMs representative of the cardiac electrical signal sensed by electrical sensing module 86 during one or more NSTs.

NST detector 126 may use techniques known in the art to determine whether a NST exists based on, for example, interval data 94. For example, NST detector 126 may determine that a particular subset of R-R interval measurements meets a predetermined NST criterion (e.g., that the average duration of the last four R-R intervals is less than 220 milliseconds). If NST detector 126 detects a NST, calculation module 128 may retrieve interval data 94, e.g., R-R interval durations, for the subset of intervals associated with the NST from NST detector 126 or memory 82.

Calculation module 128 may then calculate one or more metrics (e.g., an average, a minimum, a maximum, a range, a median, a mode, or a mean) based on the subset of interval durations, which may be the R-R interval durations associated with the NST detected by NST detector 126. Calculation module 128 may provide the calculated metric or metrics to lead integrity evaluation module 130, which may compare each metric to a predetermined threshold in order to determine whether a lead related condition exists. For example, lead integrity evaluation module 130 may compare an average NST R-R interval duration to a predetermined threshold (e.g., 220 milliseconds). If the average NST R-R interval duration is less than the predetermined threshold (i.e., less than 220 milliseconds), lead integrity evaluation module 130 may determine that a lead related condition exists. Additionally, lead integrity evaluation module 130 may require that more than one predetermined criteria is met in order to determine that a lead related condition exists. For example, lead integrity evaluation module 130 may compare each of an average, a minimum, and a range of NST R-R interval durations to respective thresholds. If, for example, an average NST R-R interval duration is less than e.g., 220 milliseconds, a minimum NST R-R interval duration is less than e.g., 160 milliseconds, and a range of NST R-R interval durations is greater than e.g., 100 milliseconds, lead integrity evaluation module 130 may determine that a lead related condition exists.

If lead integrity evaluation module 130 determines that a lead related condition exists, lead integrity evaluation module 130 may perform a therapy modification by changing therapy parameters utilized by signal generator 84. In some examples, lead integrity evaluation module 130 additionally or alternatively performs a sensing modification by changing sensing parameters utilized by electrical sensing module 86. For example, lead integrity evaluation module 130 may change a vector, e.g., change an electrode or electrodes, used by signal generator 84 for delivery of stimulation or by sensing module 86 for sensing of cardiac electrical signals. Lead integrity evaluation module 130 may stop or suspend use the vector used to sense cardiac intervals, e.g., R-R intervals, during the NST from one or both of stimulation delivery and sensing. In some examples, lead integrity module 130 additionally or alternatively modifies sensing module 86 to not use a sensing channel, e.g., amplifier, which was used to sense cardiac intervals, e.g., R-R intervals, during the NST. Alternatively or additionally, lead integrity evaluation module 130 may send a result of its evaluation to telemetry module 88. Telemetry module 88 may subsequently send the evaluation results to programmer 24 (FIG. 1) or another external device for review by a user (e.g., a clinician or patient). Additionally, if lead integrity evaluation module 130 determines that a lead related condition exists, telemetry module 88 may send an alert or a suggestion for therapy or sensing modifications to programmer 24 or another external device.

Figure 6:
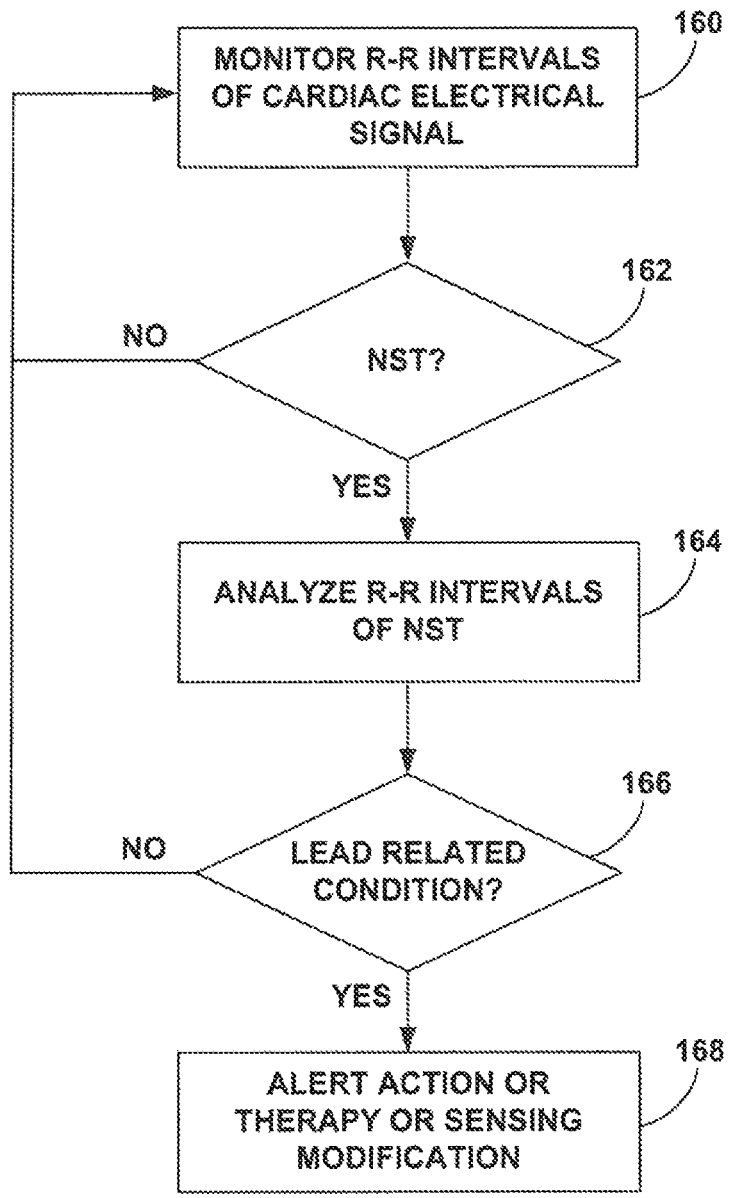
FIG. 6 is a flow diagram illustrating an example method for determining whether a lead related condition exists based on analysis of a non-sustained tachyarrhythmia (NST).

FIG. 6 is a flow diagram illustrating an example method for determining whether a lead related condition exists based on analysis of a NST cardiac electrical signal. In the illustrated example, the determination of whether a lead related condition exists is based on an evaluation of R-R intervals during an NST. In other examples, the evaluation may additionally or alternatively be based on other cardiac intervals, e.g., P-P, P-R or R-P intervals, or other aspects, e.g., morphology, of the cardiac electrical signal during the NST. Furthermore, although the example method of FIG. 6 is described as being performed by processor 80 of IMD 16, the example method may be performed by modules 124-130 (FIG. 5), and/or by any one or more devices, or processors of devices, described herein.

According to the example of FIG. 6, processor 80 (FIG. 4) monitors a cardiac electrical signal indicative of activity in heart 12 of patient 14 (FIG. 1). For example, processor 80 may measure the duration of the R-R intervals (160). Processor 80 may utilize the R-R interval duration measurements to determine whether a NST has occurred (162). If a NST has occurred, processor 80 may analyze specifically the R-R interval durations during the NST (164) to determine whether a lead related condition exists (166). If a lead related condition exists, processor 80 may send therapy or sensing modification instructions to signal generator 84, sensing module 86, or send therapy modification suggestions or an alert to programmer 24 (FIG. 1) or another external device (168).

Figure 7:
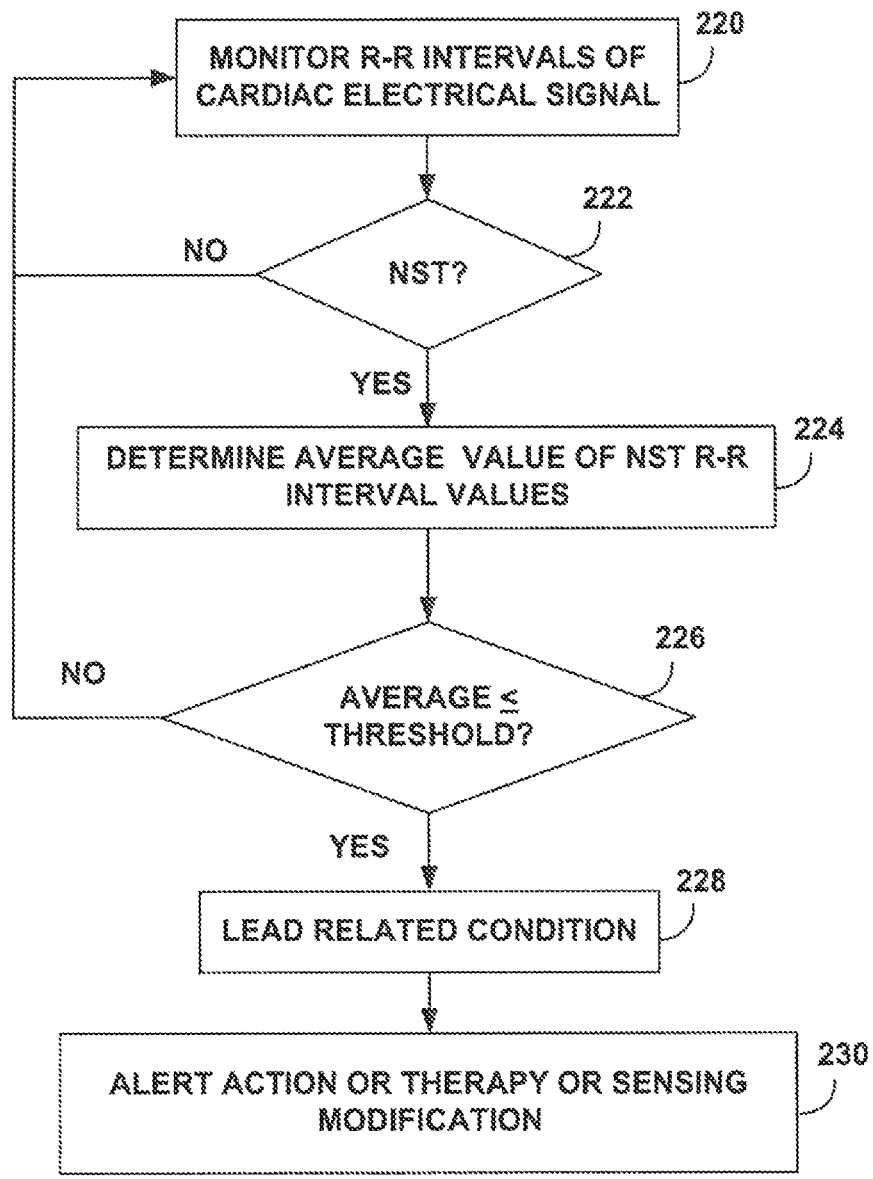
FIG. 7 is a flow diagram illustrating an example method for determining whether a lead related condition exists based on a NST R-R interval duration metric.

FIG. 7 is a flow diagram illustrating an example method for determining whether a lead related condition exists based on a NST R-R interval duration metric. In the illustrated example, the determination of whether a lead related condition exists is based on an evaluation of R-R intervals during an NST. In other examples, the evaluation may additionally or alternatively be based on other cardiac intervals, e.g., P-P, P-R or R-P intervals, or other aspects, e.g., morphology, of the cardiac electrical signal during the NST. Furthermore, although the example method of FIG. 6 is described as being performed by processor 80 of IMD 16, the example method may be performed by modules 124-130 (FIG. 5), and/or by any one or more devices, or processors of devices, described herein.

According to the illustrated example, processor 80 monitors a cardiac electrical signal indicative of activity in heart 12 of patient 14 (FIG. 1). For example, processor 80 may measure a specific type of cardiac cycle interval, such as the R-R intervals (220). NST detector 126 may analyze the R-R intervals and determine whether a NST has occurred (222). If a NST has occurred, processor 80 may calculate a metric, e.g., an average, of the NST R-R interval durations (224), and may compare the metric to a predetermined threshold (226) to determine whether a lead related condition exists based on the comparison (228). As an example, the NST criterion may require that the average NST R-R interval duration be less than (or less than or equal to) a predetermined threshold of, for example, 220 milliseconds. If this criterion is met (226), processor 80 may determine that a lead related condition exists (228), and may send therapy or sensing modification instructions to signal generator 84 or sensing module 86, or send an alert or therapy modification suggestions to programmer 24 (FIG. 1) or another external device (230).

Figure 8:
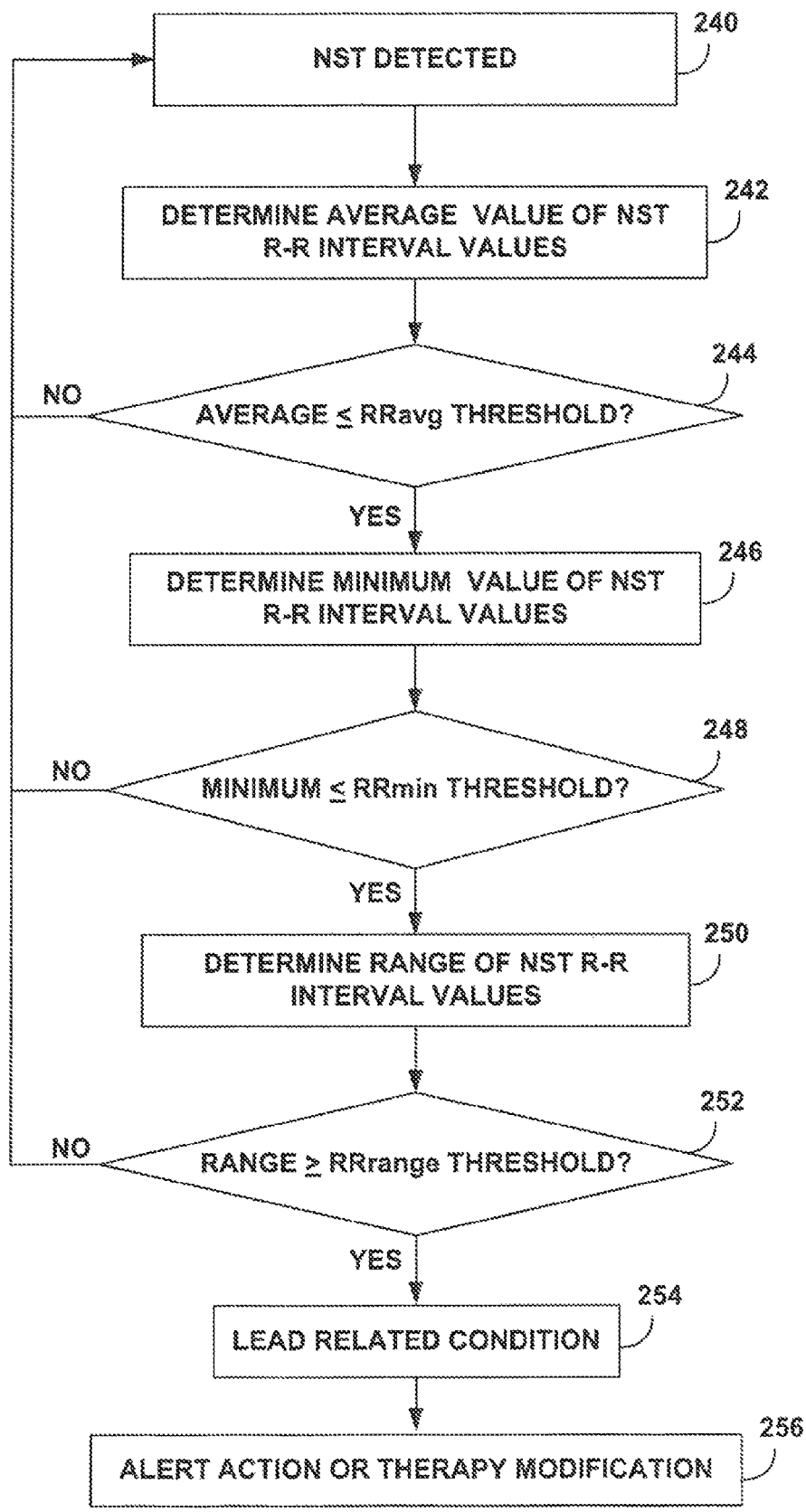
FIG. 8 is a flow diagram illustrating an example method for determining whether a lead related condition exists based on a plurality of NST R-R interval duration metrics.

FIG. 8 is a flow diagram illustrating an example method for determining whether a lead related condition exists based on more than one NST R-R interval duration metrics. In the illustrated example, the determination of whether a lead related condition exists is based on an evaluation of R-R intervals during an NST. In other examples, the evaluation may additionally or alternatively be based on other cardiac intervals, e.g., P-P, P-R or R-P intervals, or other aspects, e.g., morphology, of the cardiac electrical signal during the NST. Furthermore, although the example method of FIG. 6 is described as being performed by processor 80 of IMD 16 and modules 126-130 (FIG. 5), the example method may be performed by any one or more devices, or processors of devices, described herein. Such devices or processor may implement modules 124-130 (FIG. 5)

In the illustrated example, processor 80 monitors a cardiac electrical signal indicative of activity in heart 32 of patient 14

(FIG. 1) and determine that a NST has occurred (240). Processor 80 may then analyze the R-R interval duration measurements of the NST in order to determine if lead related condition criteria is met. For example, calculation module 128 may retrieve NST R-R interval data 94 from memory 82 or NST detector 126 (FIG. 5). Calculation module 128 may then calculate metrics such as an average, a minimum, and a range of NST R-R interval durations and compare these metrics to respective predetermined thresholds. As an example, calculation module 128 may calculate an average value of NST R-R interval values (242) and lead integrity evaluation module 130 may determine whether the calculated average value is less than (or less than or equal to) a predetermined threshold (e.g., 220 milliseconds) (244). If the average value is below the predetermined threshold, calculation module 128 may calculate a minimum value of NST R-R interval values (246) and lead integrity evaluation module 130 may determine whether the calculated minimum value is less than (or less than or equal to) a predetermined threshold (e.g., 160 milliseconds) (248). If both the average and the minimum values are is less than (or less than or equal to) the respective predetermined thresholds, calculation module 128 may calculate a range of values of NST R-R interval values (250) and lead integrity evaluation module 130 may determine whether the calculated range of values is greater than (or greater than or equal to) a predetermined threshold (e.g., 100 milliseconds) (252). If all three of the average value, the minimum value, and the range of values exceed the respective thresholds, lead integrity evaluation module 130 may determine that a lead related condition exists (254). Lead integrity evaluation module 130 may perform a therapy or sensing modification by changing therapy or sensing parameters utilized by signal generator 84 or sensing module 86 (256). Alternatively or additionally, lead integrity evaluation module 130 may send the results of its evaluation to telemetry module 88, which may send therapy modification suggestions or an alert action to programmer 24 (FIG. 1) or another external device for review by a user, e.g., a clinician or patient (256).

The R-R interval duration metrics described with respect to FIG. 8 are merely examples. Other metrics may be additionally or alternatively used in other example methods within the scope of this disclosure. Furthermore, although the example method of FIG. 8 requires satisfaction of three criteria related to three metrics prior to determining a lead related condition exists, other examples may utilize a different number of metrics and a different number of criteria.

In some examples, a device, processor, or module determines a single cardiac interval metric value, and determines whether a lead related condition exists based on the single metric value. In some examples, a device, processor, or module determines a plurality of metric values, and determines that a lead related condition exists when a single one of the plurality of metric values meets a criterion. In some examples, a device, processor, or module determines N metric values, and determines that a lead related condition exists when M of the N metric values meet respective criteria. M and N may both be greater than two, and N may be greater than M.

Furthermore, although described in the context of analysis of the cardiac electrical signals during a single NST, other examples may analyze the cardiac electrical signals for a plurality of NSTs for a determination that a lead related condition exists. In some examples, the criterion or criteria must be satisfied for M consecutive NSTs, M of the last N consecutive NSTs, or for M NSTs within a period of time, such as an hour, day, week, or month, in order for a lead related condition to be detected. In some examples, a metric, such as an average of R-R interval durations, is determined based on values collected during a plurality of NSTs, such as R-R intervals during a plurality of NSTs.

Figure 9:
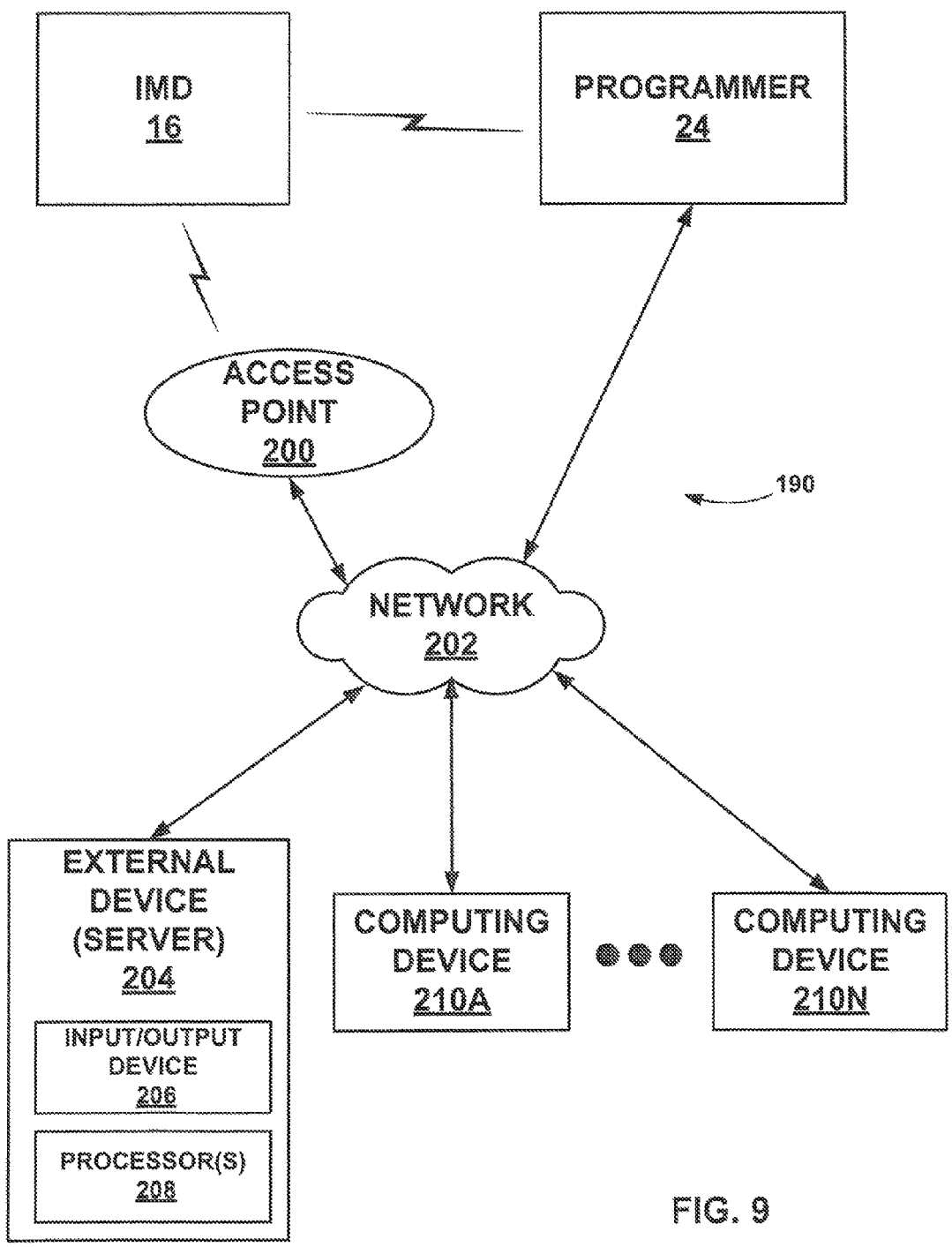
FIG. 9 is a block diagram illustrating an example system that includes an external device, such as a server, and one or more computing devices that are coupled to the IMD and programmer shown in FIG. 1 via a network.

FIG. 9 is a block diagram illustrating an example system 190 that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 9, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 9, server 204 may comprise one or more processors 208 and an input/output device 206, which need not be co-located.

Server 204 may, for example, practice the methods described herein for determining whether a lead related condition exists. Server 204 may store R-R interval data within episode data 92 maintained by server 204, detect the occurrence of a NST, and calculate metrics based on data related to the NST. Server 204 may implement any or all of the modules illustrated in FIG. 5. Furthermore, in some examples in which IMD 16 determines whether a lead related condition exists as described above, server 204 may provide a database for storing NST interval duration data within an external storage unit or memory, which may be provided by server 204 as one example, or by programmer 24 as another.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or one or more of the computing devices 210A-210N may perform any of the various functions or operations described herein.

Network 202 may comprise a local area network, wide area network, or global network, such as the Internet. In some cases, programmer 24 or server 204 may assemble episode logs 92, including EGMs 94 and 96, and other sensing integrity information in web pages or other documents for viewing by and trained professionals, such as clinicians, via viewing terminals associated with computing devices 210A-210N. System 190 may be implemented, in some aspects, with general network technology and functionality similar to that provided by the Medtronic CareLink® Network developed by Medtronic, Inc., of Minneapolis, Minn.

Although the disclosure is described with respect to cardiac stimulation therapy, such techniques may be applicable to other therapies in which sensing integrity is important, such as, e.g., spinal cord stimulation, deep brain stimulation, pelvic floor stimulation, gastric stimulation, occipital stimulation, functional electrical stimulation, and the like. In such therapies, the techniques described in this disclosure may be applied to evaluate sensing integrity and detect possible lead-related conditions.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
    detecting a plurality of cardiac events based on a cardiac electrical signal;
    measuring a plurality of intervals between consecutive ones of the detected cardiac events;
    detecting a non-sustained tachyarrhythmia based on a subset of the measured intervals meeting a non-sustained tachyarrhythmia criterion;
    after detecting the non-sustained tachyarrhythmia, calculating a plurality of metrics using the subset of the measured intervals, wherein the plurality of metrics include an average of the subset of the measured intervals, a range of the subset of the measured intervals, and a minimum of the subset of measured intervals; and
    identifying a lead related condition based on the plurality of metrics, wherein identifying the lead related condition comprises:
    comparing the average of the subset of measured intervals to a first predetermined threshold;
    comparing the minimum of the subset of measured intervals to a second predetermined threshold;
    comparing the range of the subset of measured intervals to a third predetermined threshold; and
    identifying the lead related condition when the average of the subset of measured intervals is less than the first predetermined threshold, the minimum of the subset of measured intervals is less than the second predetermined threshold, and the range of the subset of measured intervals is greater than the third predetermined threshold.

2. The method of claim 1, wherein identifying the lead related condition comprises:
    comparing each of the plurality of metrics to a respective predetermined threshold; and
    identifying the lead related condition based on the comparisons.

3. The method of claim 1, further comprising providing an alert in response to identifying the lead related condition.

4. The method of claim 1, further comprising modifying a therapy in response to identifying the lead related condition.

5. The method of claim 1, further comprising modifying at least one parameter associated with detection of the cardiac events based on detecting the lead related condition.

6. The method of claim 1, wherein the cardiac events comprise R-waves, and the intervals comprise R-R intervals.

7. A method comprising:
    detecting a plurality of cardiac events based on a cardiac electrical signal;
    measuring a plurality of intervals between consecutive ones of the detected cardiac events;
    detecting a non-sustained tachyarrhythmia based on a subset of the measured intervals meeting a non-sustained tachyarrhythmia criterion;
    after detecting the non-sustained tachyarrhythmia, calculating a plurality of metrics using the subset of the measured intervals, wherein the plurality of metrics include at least two of an average of the subset of the measured intervals, a minimum of the subset of measured intervals, and a range of the subset of the measured intervals; and
    identifying a lead related condition based on the plurality of metrics.

8. A system comprising:
    an electrical sensing module configured to receive a cardiac electrical signal from one or more electrodes and detect a plurality of cardiac events based on the cardiac electrical signal;
    an interval measurement module configured to measure a plurality of intervals between consecutive ones of the detected cardiac events;
    a non-sustained tachyarrhythmia detection module configured to detect a non-sustained tachyarrhythmia based on a subset of the measured intervals meeting a non-sustained tachyarrhythmia criterion;
    a calculation module configured to calculate a plurality of metrics based on the subset of the measured intervals after the detection of the non-sustained tachyarrhythmia, wherein the plurality of metrics include at least two of an average of the subset of the measured intervals, a minimum of the subset of measured intervals, and a range of the subset of the measured intervals; and
    identify a lead related condition based on the plurality of metrics.

9. A system comprising:
- an electrical sensing module configured to receive a cardiac electrical signal from one or more electrodes and detect a plurality of cardiac events based on the cardiac electrical signal;
- an interval measurement module configured to measure a plurality of intervals between consecutive ones of the detected cardiac events;
- a non-sustained tachyarrhythmia detection module configured to detect a non-sustained tachyarrhythmia based on a subset of the measured intervals meeting a non-sustained tachyarrhythmia criterion;
- a calculation module configured to calculate a plurality of metrics based on the subset of the measured intervals after the detection of the non-sustained tachyarrhythmia, wherein the plurality of metrics include an average of the subset of the measured intervals, a range of the subset of the measured intervals, and a minimum of the subset of measured intervals; and
- a lead integrity evaluation module configured to compare the average of the subset of measured intervals to a first predetermined threshold, compare the minimum of the subset of measured intervals to a second predetermined threshold, compare the range of the subset of measured intervals to a third predetermined threshold, and identify a lead related condition when the average of the subset of measured intervals is less than the first predetermined threshold, the minimum of the subset of measured intervals is less than the second predetermined threshold, and the range of the subset of measured intervals is greater than the third predetermined threshold.

10. The system of claim 9, further comprising a signal generator configured to deliver therapy via the one or more electrodes, and wherein the lead integrity evaluation module is configured to modify delivery of therapy by the signal generator in response to identification of the lead related condition.

11. The system of claim 9, wherein the lead integrity evaluation module is configured to:
- compare each of the plurality of metrics to a respective predetermined threshold; and
- identify the lead related condition based on the comparisons.

12. The system of claim 9, wherein the lead integrity evaluation module is configured to modify at least one parameter associated with detection of the cardiac events by the electrical sensing module based on the identification of the lead related condition.

13. The system of claim 9, further comprising a telemetry module configured to transmit information regarding at least one of an alert, a therapy modification, or a sensing modification if a lead related condition exists.

14. The system of claim 9, wherein the non-sustained tachyarrhythmia detection module is configured to identify a plurality of events in the cardiac electrical signal as cardiac depolarizations, determine a rate of at least some of the events, and detect the non-sustained tachyarrhythmia based on the rate.

15. The system of claim 9, wherein the cardiac events comprise R-waves, and the intervals comprise R-R intervals.

16. The system of claim 9, further comprising an implantable medical device that comprises the electrical sensing module, the interval measurement module, the non-sustained tachyarrhythmia detection module, the calculation module, and the lead integrity evaluation module.

17. A system comprising:
- means for detecting a plurality of cardiac events based on a cardiac electrical signal;
- means for measuring a plurality of intervals between consecutive ones of the detected cardiac events;
- means for detecting a non-sustained tachyarrhythmia based on a subset of the measured intervals meeting a non-sustained tachyarrhythmia criterion;
- means for calculating a plurality of metrics based on the subset of the measured intervals after detecting the non-sustained tachyarrhythmia, wherein the plurality of metrics include an average of the subset of the measured intervals, a range of the subset of the measured intervals, and a minimum of the subset of measured intervals; and
- means for identifying a lead related condition based on the plurality of metrics, wherein the means for identifying the lead related condition:
  - compares the average of the subset of measured intervals to a first predetermined threshold;
  - compares the minimum of the subset of measured intervals to a second predetermined threshold;
  - compares the range of the subset of measured intervals to a third predetermined threshold; and
  - identifies the lead related condition when the average of the subset of measured intervals is less than the first predetermined threshold, the minimum of the subset of measured intervals is less than the second predetermined threshold, and the range of the subset of measured intervals is greater than the third predetermined threshold.

18. A non-transitory computer readable storage medium comprising instructions that, when executed, cause a processor to:
- detect a plurality of cardiac events based on a cardiac electrical signal;
- measure a plurality of intervals between consecutive ones of the detected cardiac events;
- detect a non-sustained tachyarrhythmia based on a subset of the measured intervals meeting a non-sustained tachyarrhythmia criterion;
- after detecting the non-sustained tachyarrhythmia, calculate a plurality of metrics based on the subset of the measured intervals, wherein the plurality of metrics include an average of the subset of the measured intervals, a range of the subset of the measured intervals, and a minimum of the subset of measured intervals;
- compare the average of the subset of measured intervals to a first predetermined threshold;
- compare the minimum of the subset of measured intervals to a second predetermined threshold;
- compare the range of the subset of measured intervals to a third predetermined threshold; and
- identify a lead related condition, when the average of the subset of measured intervals is less than the first predetermined threshold, the minimum of the subset of measured intervals is less than the second predetermined threshold, and the range of the subset of measured intervals is greater than the third predetermined threshold.

* * * * *